(12) United States Patent
Tervamäki et al.

(10) Patent No.: US 6,372,504 B1
(45) Date of Patent: Apr. 16, 2002

(54) METHOD AND APPARATUS FOR CONVEYING A SAMPLE TO A SAMPLE VESSEL

(75) Inventors: Jukka Tervamäki; Jukka Tuunanen; Jouko Mikkonen, all of Helsinki (FI)

(73) Assignee: Labsystems Oy, Helsinki (FI)

( * ) Notice: Subject to any disclaimer, the term of this patent is extended or adjusted under 35 U.S.C. 154(b) by 0 days.

(21) Appl. No.: 09/405,168

(22) Filed: Sep. 24, 1999

(30) Foreign Application Priority Data

Dec. 16, 1998 (FI) .................................................. 982720

(51) Int. Cl.$^7$ .............................................. G01N 35/02
(52) U.S. Cl. ............................ 436/48; 422/56; 422/66; 422/68.1
(58) Field of Search ....................... 422/56, 66, 68.1; 436/47, 48

(56) References Cited

U.S. PATENT DOCUMENTS

| | | | |
|---|---|---|---|
| 4,341,735 A | | 7/1982 | Seifried ...................... 422/66 |
| 5,146,794 A | | 9/1992 | Rising et al. ............. 73/864.41 |
| 5,460,057 A | * | 10/1995 | Ostrup ..................... 73/864.81 |
| 5,474,742 A | * | 12/1995 | Tuuminen .................... 422/63 |
| 5,510,081 A | * | 4/1996 | Edwards et al. ............... 422/63 |
| 5,638,170 A | * | 6/1997 | Trinka et al. ................ 356/244 |
| 5,641,682 A | * | 6/1997 | Pagels et al. ................. 436/43 |
| 5,862,729 A | * | 1/1999 | Rolon et al. .................... 83/23 |

FOREIGN PATENT DOCUMENTS

FI  923220  7/1992

* cited by examiner

Primary Examiner—Nina Bhat
(74) Attorney, Agent, or Firm—Burns, Doane, Swecker & Mathis, L.L.P.

(57) ABSTRACT

Conveying of a sample disk method and apparatus for into a reaction vessel is described wherein the sample disk (11) is attached to a tooth (2), where the sample disk is further conveyed to the reaction vessel.

22 Claims, 2 Drawing Sheets

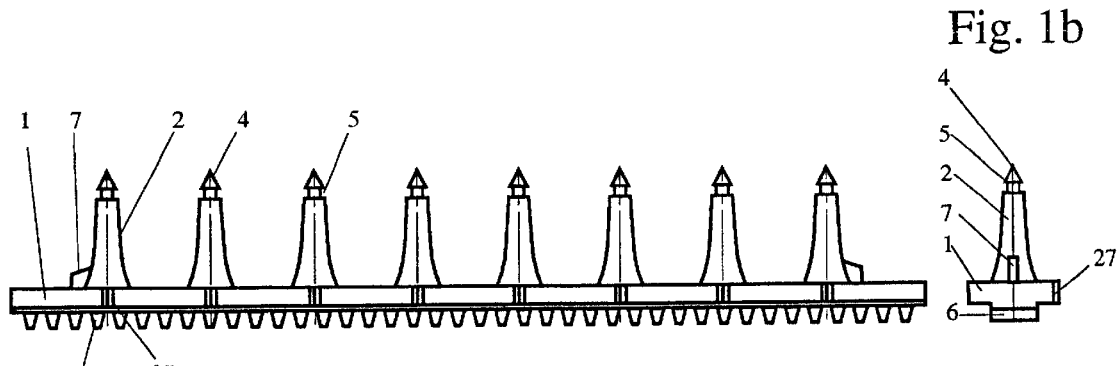
Fig. 1b
Fig. 1a
Fig. 1c
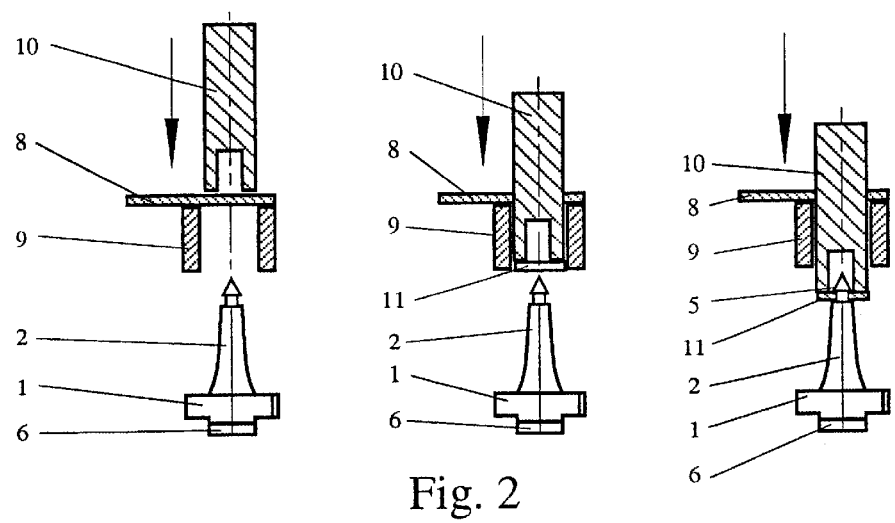
Fig. 2
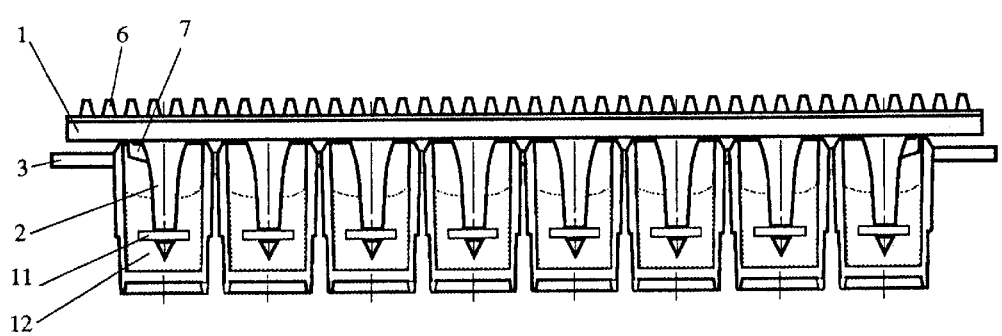
Fig. 3

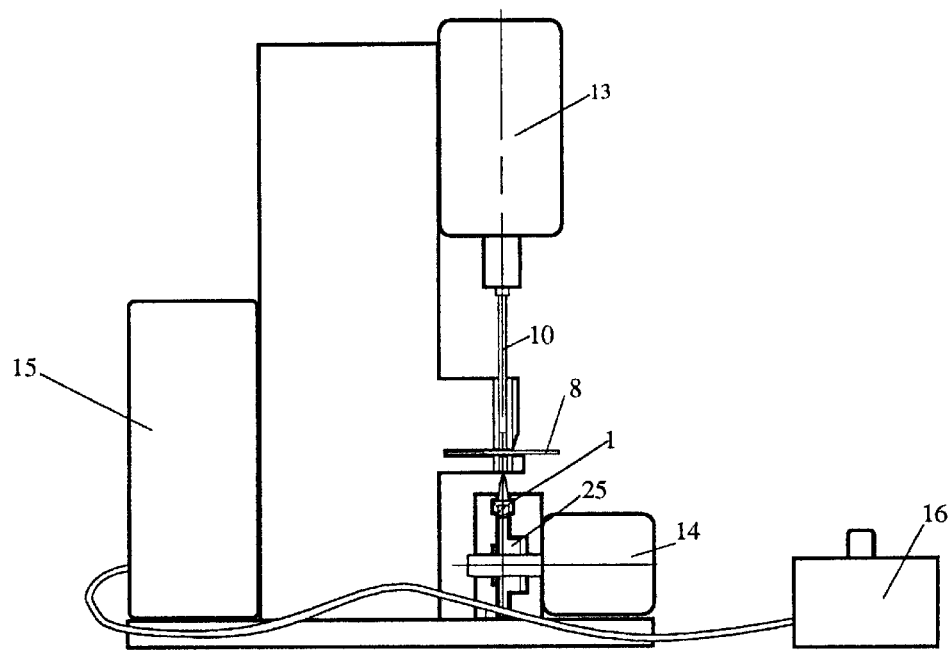
Fig.4
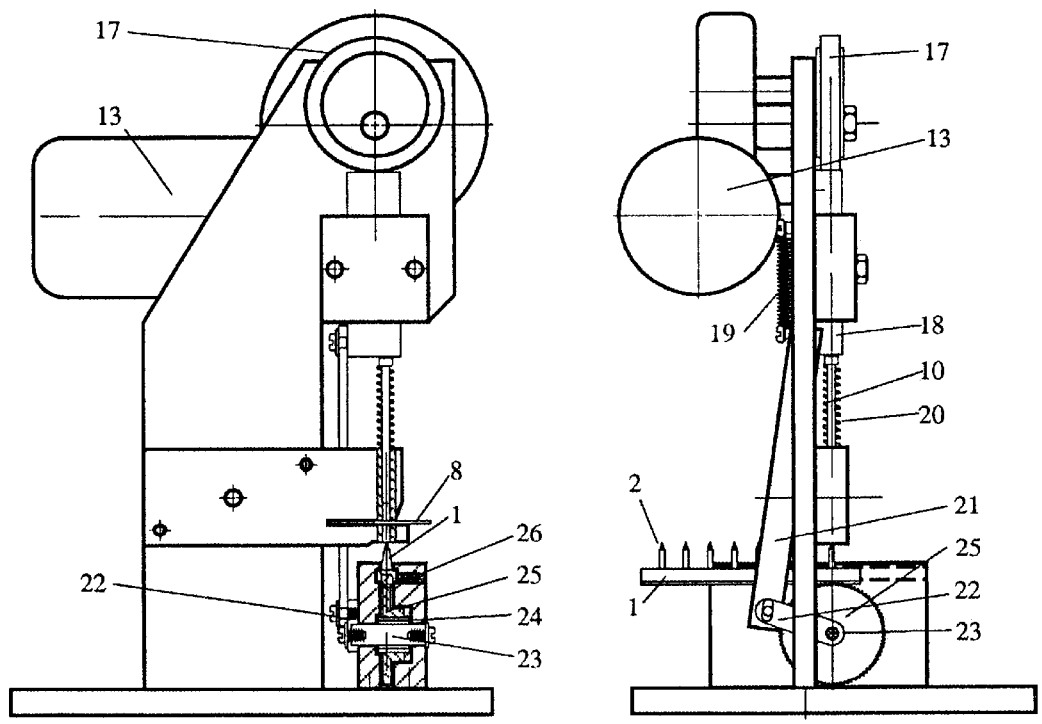
Fig.5a
Fig.5b

METHOD AND APPARATUS FOR CONVEYING A SAMPLE TO A SAMPLE VESSEL

BACKGROUND OF THE INVENTION

The present invention relates to laboratory technology and in particular to a method of analysis where in a porous, sheet-like material, such as filter paper, there is absorbed a sample, such as a specimen of dried blood, of which material there is cut a disk, which disk is then conveyed to a vessel or a vessel matrix, such as a set of test tubes or cuvettes, where the sample disk is eluted. After elution, the sample disk can be removed, and the obtained solution is subjected to the analysis in question.

In the above described tasks for conveying a sample disk into a reaction vessel and for removing it therefrom, there are generally used a pair of tweezers, and the method requires a lot of manual work. The analyses are usually carried out in series, for instance on a microtitration plate, in which case the analysis is made simultaneously in each well of the plate. The U.S. patent publication 5,474,742 introduces an apparatus whereby sample disks can be simultaneously inserted in and removed from all wells on the plate. The apparatus comprises a framework with arms for each well, and the bottom part of each arm is provided with a shelf-like sample disk retainer.

The method and apparatus according to the invention is designed to facilitate and speed up the conveying of samples of the described type in and out of the vessel of analysis.

DESCRIPTION OF THE INVENTION

We have now invented a method and apparatus according to the independent claims. Other claims represent a few preferred embodiments of the invention.

According to the invention, a sample disk is attached to a tooth, where it is conveyed to the reaction vessel. The sample disk can also be removed from the vessel by the tooth. One rack may contain several teeth, corresponding to the pitch of the cuvettes provided in the plate used in the analysis, which further facilitates the task of performing several analyses in series.

A tooth may include a sharp, cutting part, in which case the tooth penetrates the sheet with as little damage as possible. Moreover, the tooth may include barbs in order to improve the grip.

A sample disk can be cut of a larger sheet, for instance by punching it directly onto the tooth. In this fashion, less steps are needed in the process. The punching is advantageously carried out by pushing the punching tool downwardly, against the sample sheet.

The apparatus may include means for shifting the tooth rack, preferably automatically, for the length of a tooth interval at a time. The apparatus may also include means for ensuring an accurate position for the shifted rack.

In order to shift the rack, it may contain a suitable grip member, such as an indentation.

A combined sample disk punching and fastening can be realized by means of separate actuators, or by means of one and the same actuator.

A preferred embodiment of the present invention is explained in more detail below. The accompanying drawings form part of the description. In the drawings FIG. 1a illustrates a tooth rack according to the invention, seen from the side to the teeth of which rack the sample disks are attached, FIG. 1b illustrates the tooth rack of FIG. 1a from the end, FIG. 1c illustrates one tooth of the rack of FIG. 1a from the top, FIG. 2 illustrates the different stages of attaching the sample disk to the tooth, FIG. 3 illustrates a tooth rack installed in a set of cuvettes, FIG. 4 illustrates an apparatus according to the invention, provided with separate actuators for attaching the sample disk and for moving the tooth rack, FIG. 5a illustrates from the side an apparatus according to the invention, provided with only one actuator both for attaching the sample disk and for moving the tooth rack, and FIG. 5b illustrates the apparatus of FIG. 5a from the end.

FIGS. 1a to 1c illustrate a comb-like straight strip 1, provided with vertical teeth 2 spaced according to the pitch of the test tube or cuvette matrix 3 (FIG. 3). The number of teeth 2 corresponds for example to the number of the wells in a row of the plate, for instance a microtitration plate. Each tooth head is advantageously designed so that it includes a sharp, paper-cutting peak 4, and hooking barbs 5 on opposite sides. In the longitudinal direction of the barbs, the peak of the tooth 2 is somewhat longer than in the transversal direction thereof. The strip 1 can be provided with an indentation 6 or other gripping or shifting member needed for the transfer, as well as with centering means 7 for centering the strip 1 in the cuvette matrix 3.

FIG. 2 illustrates how in the method according to the invention, a filter paper 8 or other porous plate saturated with a sample is set on top of a punching bed 9, whereafter the user either pulls the lever of a manually operated device, or presses the button or pedal (16) of an automatic device (FIG. 4, FIG. 5a), in which case the punching tool 10 cuts out of the paper 8 a sample, most advantageously a round sample 11, shifts it towards the tooth 2, which penetrates the paper 11 simultaneously as the barbs 5 fasten the sample disk 11 onto the tooth 2. Thereafter the punching tool 10 returns to the top position, and the strip 1 can be shifted, either manually or automatically, by means of a grip member such as an indentation 6, forward for the length of an interval according to the pitch of the teeth, as far as the next tooth, and the next cutting step may begin.

FIG. 3 illustrates how a matrix formed of the teeth 2 of the strip 1 is partly or completely loaded with sample disks 11 and turned upside down to a cuvette matrix 3, in which case the sample disks 11 are submerged in the elution liquid or reagent 12, and the sample of the desired material, such as blood ore serum, is removed from the sample disk. The centering means 7 center the teeth 2 in the cuvette matrix 3. After elution, the strip complete with sample disks 11 can be easily removed.

FIG. 4 illustrates a preferred embodiment of an automatic punching and conveying device. There an actuator 13, for instance a spindle motor or a pneumatic cylinder, moves a cutting punching tool 10, and another actuator 14, for instance a stepping motor, moves the strip 1 by intermediation of a gear wheel 25. Each actuator can be either electric, such as a magnet, a stepping motor or a spindle motor, or alternatively a pneumatic or a hydraulic cylinder or motor. The cutting and the moving of the strip 1 is synchronized by means of a electronic card or a control unit 15, which is connected to a press button or foot pedal 16 for starting the cutting process.

FIGS. 5 and 5b illustrate a preferred embodiment of an automatic device which is provided with only one motor 13 or other actuator, whereby both the cutting of the paper 8 and the conveying of the strip 1 are performed. For instance a gear motor 13 rotates a cam 17, which further presses the punching tool 10 downwardly by intermediation of a lever 18. The lever 18 is returned to the top position by means of a lever spring 19, and the punching tool 10 is returned by means of a punching tool spring 20.

To the lever 18, there is geared a push bar 21, the bottom end whereof moves the bent lever 22 back and forth. The bent lever 22 is attached to shaft 23, and said shaft 23, along with its alternating motion, during the return motion of the push bar 21 pulls the gear wheel 25 by intermediation of a one-way clutch 24, and the gear wheel further moves the strip 1 by means of the indentation 6 provided therein. Thus the one-way clutch 24 ensures that the gear wheel 25 and the strip 1 only move in one direction. The length of the bent lever 22 and the diameter of the gear wheel 25 are chosen so that the strip 1 moves, during the alternating motion of the lever 18, exactly for the length of the pitch of the teeth 2. A spring-loaded ball 26 is slipped in the notches 27 provided at the side of the strip 1, thus ensuring that the strip 1 is stopped at a point which corresponds to the pitch of the teeth 2.

Instead of the lever 18, the apparatus may be provided with a vertical slide.

The tooth rack 1 can also be provided with a position sensor, for example a hole at the other end thereof, which ensures that the rack is put in the device in the correct position, and that the order of the sample disks attached in the teeth 2 of the comb is known, as well as the corresponding order of patients.

What is claimed is:

1. A method for conveying a sample disk to a reaction vessel, comprising attaching the sample disk to a tooth on a rack, conveying the rack with the tooth and the sample disk to the reaction vessel, and inserting the tooth into the reaction vessel.

2. A method according to claim 1, wherein the sample disk is cut of a larger sheet.

3. A method according to claim 2, wherein the sample disk is attached by cutting it directly onto the tooth.

4. A method according to claim 2, wherein the sample disk is cut by punching.

5. A method according to claim 1, for conveying a sample disk containing a specimen of blood or serum.

6. An apparatus for conveying a sample disk to a reaction vessel, wherein the sample apparatus comprises a rack provided with a tooth for fastening the sample disk, the rack being adapted to be conveyed to the reaction vessel for insertion of the tooth into the reaction vessel.

7. An apparatus according to claim 6, wherein the rack (1) is provided with a plurality of teeth (2) for fastening sample disks.

8. An apparatus according to 7, wherein the rack is provided with teeth (2) sin a row.

9. An apparatus according to claim 8, wherein the teeth (2) are at a constant pitch.

10. An apparatus according to claim 9, wherein the apparatus comprises means (14; 25) for shifting the rack for a length according to the pitch.

11. An apparatus according to claim 10, wherein the apparatus comprises means (14; 25) for shifting the rack automatically.

12. An apparatus according to claim 6, wherein the tooth has a sharp peak (4).

13. An apparatus according to claim 12, wherein the tooth has barbs (5) for fastening the sample disk.

14. An apparatus according to claim 6, wherein the tooth has a cutting peak (4).

15. An apparatus according to claim 6, wherein the apparatus comprises cutting means for cutting the sample disk of a larger sheet and for shifting the sample disk toward the tooth after being cut from the larger sheet.

16. An apparatus according to claim 15, wherein the cutting means comprises a punching tool for punching the sample disk of the larger sheet.

17. An apparatus according to claim 15, wherein the apparatus comprises one motor, said motor for conveying the rack to the reaction vessel and cutting of the sample disk from the larger sheet by the cutting means.

18. An apparatus according to claim 17, wherein the rack is comblike, the apparatus comprising:

a one way clutch; and a gear wheel;

wherein the cutting means comprises a punching tool which works with an alternating motion, so that from the alternating motion of the punching tool, there is provided lever transmission through the one-way clutch to the gear wheel, the gear wheel moving the comb-like rack forward in a stepping fashion.

19. An apparatus according to claim 6, wherein the rack comprises grip members for conveying the rack to the reaction vessel.

20. An apparatus according to claim 19, wherein the grip members comprise an indentation on the rack for conveying the rack to the reaction vessel.

21. An apparatus according to claim 6, wherein the apparatus comprises positioning means in the rack and at a side of the rack for ensuring an accurate position of the rack during forward conveying of the rack.

22. An apparatus according to claim 21, wherein the positioning means comprises notches located at a side of the rack and a spring-loaded ball for engaging the notches.

\* \* \* \* \*